(12) United States Patent
Nir

(10) Patent No.: US 6,785,570 B2
(45) Date of Patent: Aug. 31, 2004

(54) SYSTEM AND METHOD FOR ANALYSIS OF A TISSUE

(75) Inventor: Dror Nir, Matan (IL)

(73) Assignee: MD Medical Diagnostics Inc., Wilmington, DE (US)

(*) Notice: Subject to any disclaimer, the term of this patent is extended or adjusted under 35 U.S.C. 154(b) by 35 days.

(21) Appl. No.: 09/874,919

(22) Filed: Jun. 5, 2001

(65) Prior Publication Data

US 2002/0115924 A1 Aug. 22, 2002

Related U.S. Application Data

(60) Provisional application No. 60/258,182, filed on Dec. 22, 2000.

(51) Int. Cl.⁷ ............................................. A61B 5/00
(52) U.S. Cl. ................................. 600/407; 600/437
(58) Field of Search ............................. 600/437, 443, 600/447; 382/6, 128, 132

(56) References Cited

U.S. PATENT DOCUMENTS

| | | | | |
|---|---|---|---|---|
| 4,453,550 A | * | 6/1984 | Flax | 600/437 |
| 4,655,228 A | * | 4/1987 | Shimura et al. | 73/602 |
| 4,803,994 A | * | 2/1989 | Burke | 600/442 |
| 4,817,015 A | * | 3/1989 | Insana et al. | 600/437 |
| 4,851,984 A | * | 7/1989 | Doi et al. | 382/6 |
| 4,858,124 A | * | 8/1989 | Lizzi et al. | 73/602 |
| 5,081,993 A | | 1/1992 | Kitney et al. | 128/661.08 |
| 5,107,841 A | | 4/1992 | Sturgill | 128/661.09 |
| 5,319,549 A | * | 6/1994 | Katsuragawa et al. | 382/6 |
| 5,524,636 A | | 6/1996 | Sarvazyan et al. | 128/774 |
| 5,651,363 A | * | 7/1997 | Kaufman et al. | 600/438 |
| 5,839,441 A | | 11/1998 | Steinberg | 128/660.04 |
| 5,982,917 A | * | 11/1999 | Clarke et al. | 382/132 |
| 6,234,968 B1 | | 5/2001 | Sumanaweera et al. | 600/443 |
| 6,282,305 B1 | * | 8/2001 | Huo et al. | 382/128 |
| 6,312,382 B1 | | 11/2001 | Mucci et al. | 600/437 |
| 6,317,617 B1 | * | 11/2001 | Gilhuijs et al. | 600/443 |
| 240,187 A1 | | 4/2002 | Alam et al. | 600/442 |

* cited by examiner

Primary Examiner—Francis J. Jaworski
(74) Attorney, Agent, or Firm—Ladas & Parry

(57) ABSTRACT

A method and system for assessing a spatial regularity of reflecting members in a tissue. The method comprises irradiating the tissue and detecting waves reflected by the tissue. One or more parameters are then calculated, based upon the reflected waves, indicative of a degree of spatial disorder of reflecting members in the tissue.

16 Claims, 5 Drawing Sheets

HEALTHY

MALIGNANT

BENIGN

SYSTEM AND METHOD FOR ANALYSIS OF A TISSUE

This application claims the benefit of provisional application No. 60/258,182, filed Dec. 22, 2000.

FIELD OF THE INVENTION

This invention relates to methods for analyzing data obtained by irradiating biological tissues or organs.

BACKGROUND OF THE INVENTION

Imaging methods such as ultrasound (US), magnetic resonance imaging (MRI), and computer tomography (CT), are widely used because of their ability to non-invasively image body organs and tissues with minor deleterious effects. In these techniques, an organ or tissue is irradiated with sonic or electromagnetic waves. The waves reflected or scattered by the organ or tissue are recorded and processed into a digital image.

SUMMARY OF THE INVENTION

The present invention is based upon the finding that healthy tissue may be distinguished from its malignant counterpart by the way the tissue reflects radiation energy. The organization of reflecting members in a healthy tissue is more spatially regular than in malignant tissue. The invention may thus be used in the diagnosis of cancer or other disorders involving alterations in the organization or texture of a tissue, such as the presence of a liquid filled cyst.

In accordance with the invention, a tissue is irradiated and the reflected waves are detected. An analysis is performed on the reflected waves in order to generate one or more parameters indicative of a degree of spatial disorder of the reflecting members in the tissue. In one embodiment of the invention, a calculated parameter value is compared to a predetermined threshold. If the calculated parameter value exceeds the threshold, the tissue is determined to be malignant. A tissue having a calculated parameter value less than the threshold is a healthy tissue. In another embodiment, one or more calculated parameters are input to an expert system such as a neural network. The neural system makes an assessment as to whether the tissue is healthy or malignant based upon the input parameter values. Expert systems are known, for example as disclosed in Kadah et al., IEEE Transactions, vol. 15, No. 4, pages 472–473, 476–477, August 1996.

The invention may be carried out using any form of irradiation such as electromagnetic radiation or sonic radiation. In particular, the invention may be applied to waves reflected in an ultrasound, CT, or MRI procedure.

The analysis of the detected reflected waves may be performed using any mathematical method for evaluating a degree of periodicity. The analysis may thus involve, for example, a Fourier analysis, a wavelet analysis, or an entropy analysis. The analysis may be performed on complex raw data obtained from the reflected waves. Alternatively, an image may be generated from the complex raw data, and the analysis performed on the image.

In another of its aspects, the invention provides a method for generating an image of the tissue based upon the reflected or scattered waves using non-Fourier analysis. This produces an image of better resolution and contrast than is obtainable by a Fourier analysis of the reflected or scattered waves, which is the present standard of existing signal processing algorithms. Methods for non-Fourier analysis of scattered or reflected waves are known in the art, for example, as disclosed in Degraaf, S., IEEE Transactions on Image Processing, Vol. 7, No. 5, May 1998. As shown in this reference, the non-Fourier analysis may utilize for example, Capon's minimum variance method.

Thus in its first aspect, the invention provides a method for assessing a spatial regularity of reflecting members in a tissue, comprising steps of:
 (a) irradiating the tissue;
 (b) detecting waves reflected by the tissue; and
 (c) calculating one or more parameters indicative of a degree of spatial disorder of reflecting members in the tissue based upon the reflected waves.

In its second aspect, the invention provides, a method for determining whether a tissue is malignant comprising steps of;
 (a) irradiating the tissue;
 (b) detecting waves reflected by the tissue;
 (c) calculating a parameter indicative of a degree of spatial disorder of reflecting members in the tissue based upon the reflected waves; and
 (d) comparing the parameter to a predetermined threshold; the tissue being malignant if the parameter exceeds the predetermined threshold.

In its third aspect, the invention provide a method for determining whether a tissue is malignant comprising steps of;
 (a) irradiating the tissue;
 (b) detecting waves reflected by the tissue;
 (c) calculating one or more parameters indicative of a degree of spatial disorder of reflecting members in the tissue based upon the reflected waves; and
inputting the one or more parameters into an expert system so as to generate an assessment as to whether the tissue is malignant.

In its fourth aspect, the invention provides a system for assessing a spatial regularity of reflecting members in a tissue, comprising:
 (a) a wave source configured to irradiate the tissue;
 (b) a wave detector configured to detect waves reflected by the tissue; and;
 (c) a processor configured to calculate a parameter indicative of a degree of spatial disorder of reflecting members in the tissue based upon the reflected waves.

In its fifth aspect, the invention provides, a system for determining whether a tissue is malignant comprising:
 (a) a wave source configured to irradiate the tissue;
 (b) a wave detector configured to detect waves reflected by the tissue;
 (c) a processor configured to calculate a parameter indicative of a degree of spatial disorder of reflecting members in the tissue based upon the reflected waves.

In its sixth aspect, the invention provides a method for determining whether a tissue is malignant comprising steps of;
 (a) irradiating the tissue;
 (b) detecting waves reflected or scattered by the tissue;
 (c) performing an analysis of the reflected or scattered waves;
 (d) inputting the results of the analysis into an expert system.

In yet another aspect, the invention provides a method for generating an image of the tissue, comprising steps of:

(a) irradiating the tissue;

(b) detecting waves reflected by the tissue; and performing a non-Fourier analysis of the detected waves so as to produce an image of he tissue.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
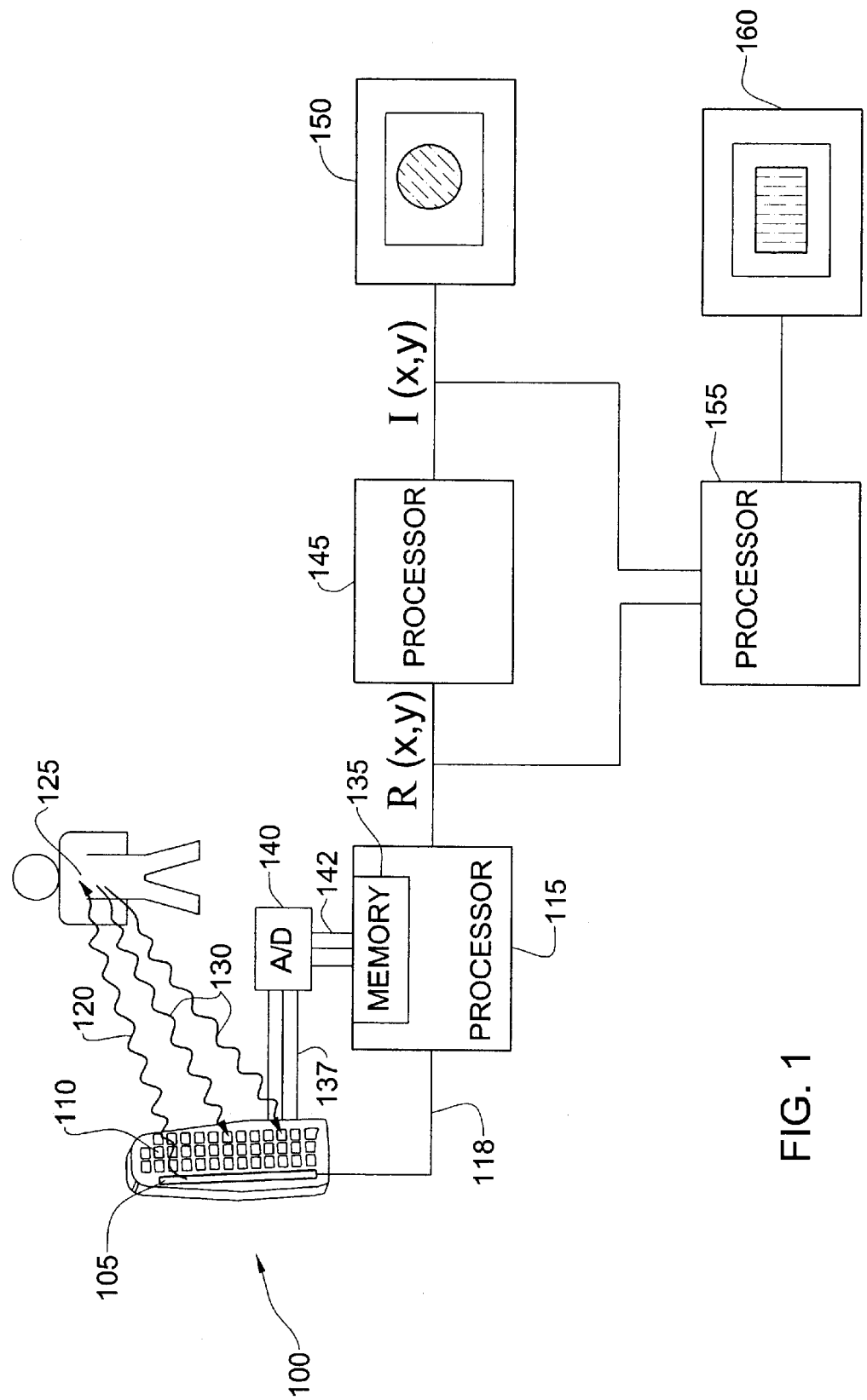
FIG. 1 shows a system for analyzing reflected waves in accordance with one embodiment of the invention.
Figure 2A:
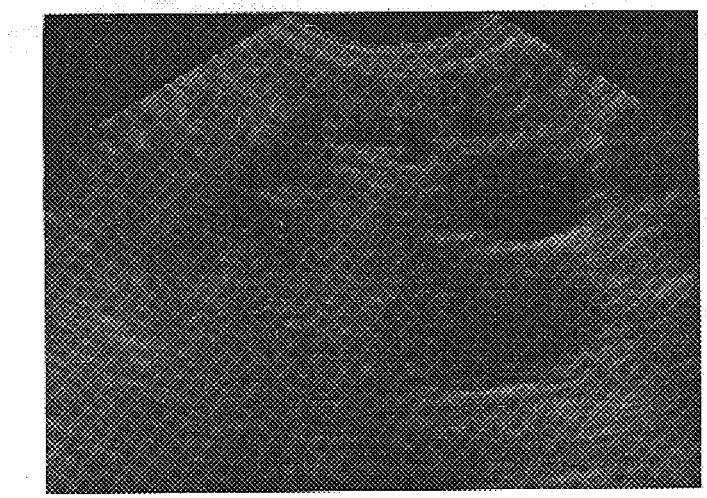
FIG. 2 shows a Fourier analysis of healthy (a,d), malignant (b,e) and benign (c,f) ovarian tissue in accordance with one embodiment of the invention.
Figure 2B:
Figure 2C:
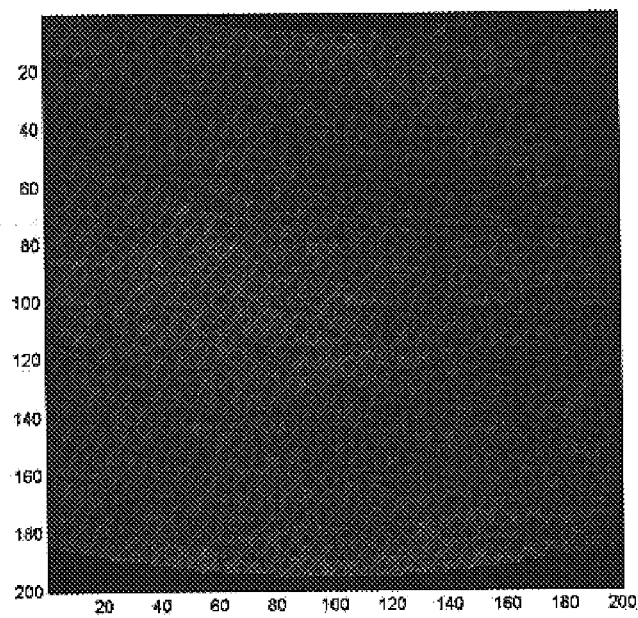
Figure 2D:
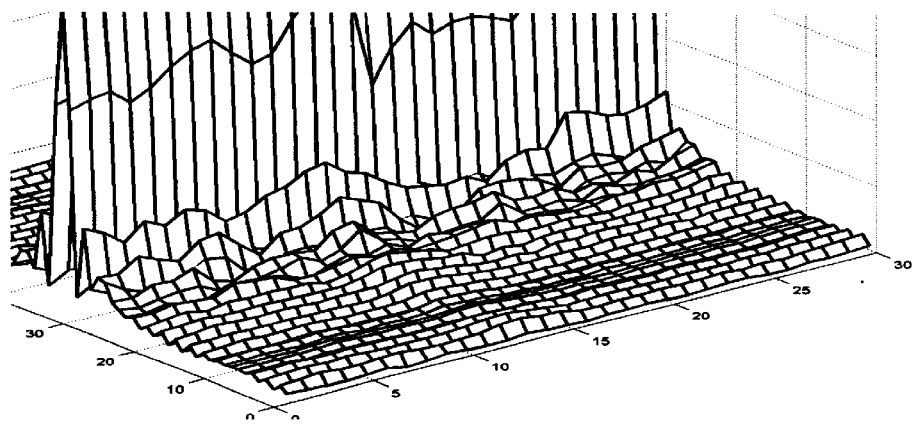
Figure 2E:
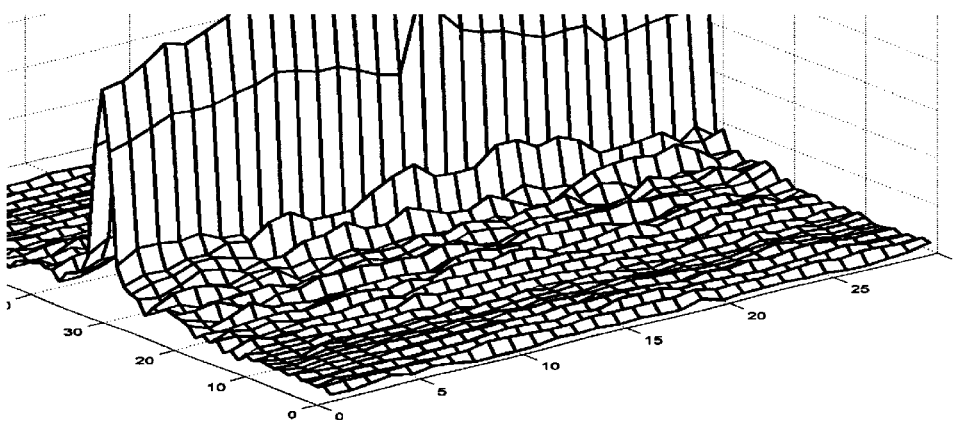
Figure 2F:
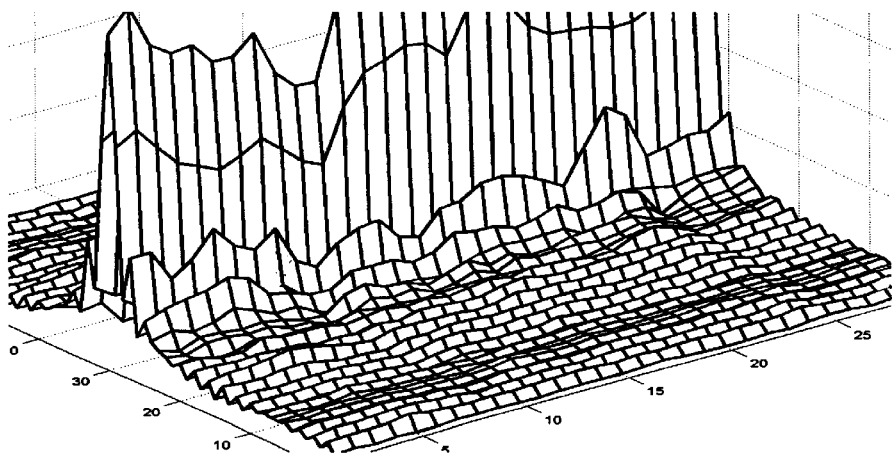

FIG. 1 shows a system for analyzing biological tissues or organs in accordance with one embodiment of the invention. A transducer 100 contains a wave generator 105 for generating waves. The generated waves may be sonic waves or electromagnetic waves. The transducer also comprises an array of detectors 110 that detect reflected waves. A processor 115 is used to select the properties of the generated waves (e.g. amplitude and wavelength) via a signal 118 input to the wave generator 105. The wave generator 105 is used to produce generated waves 120 that irradiate a tissue or organ 125. Waves 130 reflected by the organ or tissue 125 are detected by the detectors 110 in the transducer 105. The wave detected by each detector is converted by the detector into an analog voltage dependent signal that is sampled by an analog to digital converter 140. The digital samples 142 are then input to the processor 115. The processor 115 calculates a phase for each sample based upon the signal 118 and stores the digital samples in a memory 135 in the form of complex raw data R(x,y).

A second processor 145 is configured to receive the complex raw data R(x,y) from the memory 135 and process the complex raw data into an image I(x,y) as is known in the art. The image may be displayed on a display such as a CRT 150.

In accordance with the invention, a third processor 155 is configured to analyze the tissue by processing either the raw data R(x,y) or the processed image data I(x,y). The results of the analysis may be displayed on a display such as the CRT 160.

EXAMPLES

Example 1

Fourier Analysis of Ultrasound Images

FIG. 2 shows an ultrasound image I(x,y) of human ovary tissue from a healthy ovary (a) from a malignant ovarian tumor (b), and a benign ovarian tumor (c), as determined by histological examination of the tissues. (e) (f) and (g) show the Fourier transform $F(y,\omega) = \int I(x,y)e^{i\omega x}dx$ of a 30×30 pixel square from the image shown in (a) (b) and (c), respectively. The energy of each Fourier transform was measured by evaluating the sum $\Sigma |\partial FI \partial y|$ over the range of $1 \leq y \leq 28$ and $34 \leq \omega \leq 64$. The energy calculated for the normal tissue (a,d) was 3, for the malignant tissue (b,e) 8, and for the benign tissue, 3. An analysis of 30 ovarian tissue showed that by this method of calculating energy, healthy ovarian tissues have an energy in the range of about 2 to 4, while malignant ovarian tissues have an energy in the range of about 7–9. Ovarian tissues having a benign growth were indistinguishable from healthy ovarian tissues. Other methods may be used for measuring energy may also be used in accordance with the invention such as calculating a volume under the Fourier transform.

Example 2

Wavelet Analysis of Ultrasound Images

Figure 3A:
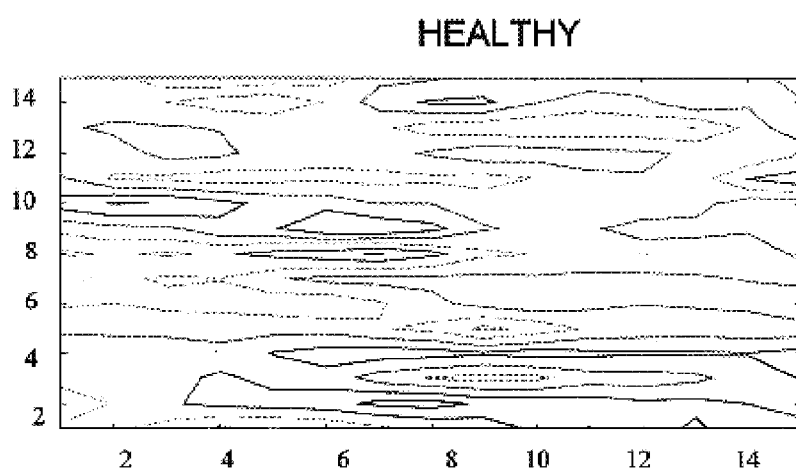
FIG. 3 shows a wavelet analysis of healthy (a); malignant (b); benign (c) ovarian tissue, in accordance with another embodiment of the invention.
Figure 3B:
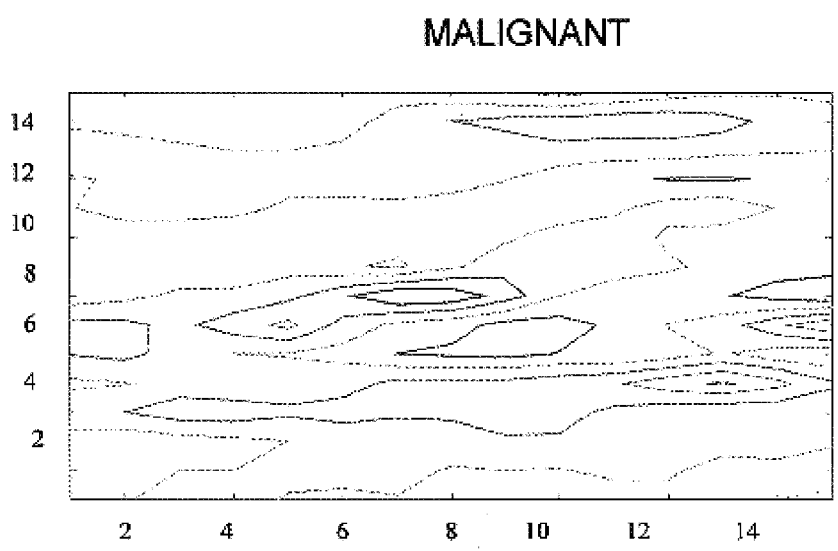
Figure 3C:
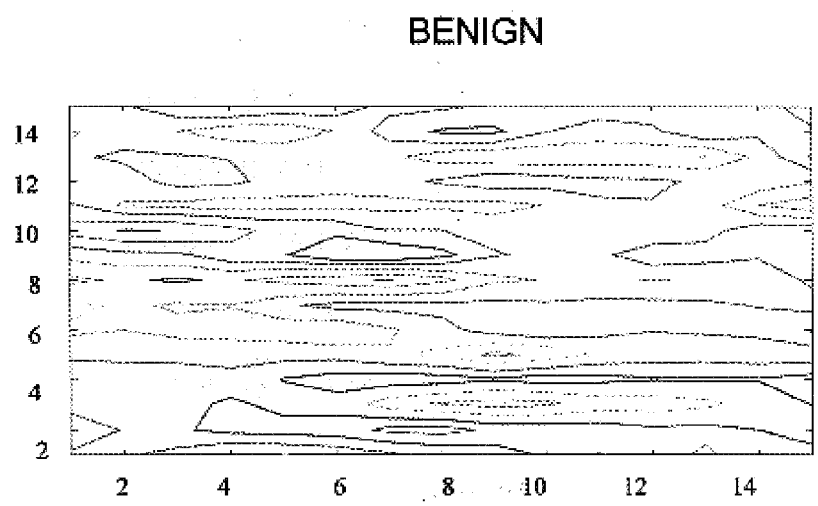

FIG. 3 shows a wavelet analysis of the three images I(x,y) shown in FIG. 2. The 30×30 pixel square from each image was input to the wavelet analysis software of the Matlab™ wavelet toolbox. The B-orthogonal filter was used with a decomposition level equal to 1. The output of this software is four matrices known as the principle image coefficients (A), horizontal coefficients (H), vertical image coefficients (V) and the diagonal coefficients (D). FIG. 3 shows the contour graph of the coefficients of the A matrix obtained for each image. The maximum of each contour graph was used as an index. The index of the malignant tissue is 204, of the benign tissue 162 and the healthy tissue 90. An analysis of 30 ovarian tissues showed that malignant tissues have indices 2–2.5 times those of healthy tissues. Other indices maybe be also used in accordance with the invention when using wavelet analysis such as the maximum coefficient in sum of the H, V, and D coefficient matrices. Other filters may be used in accordance with the invention such as a Mexican hat filter, as are known in the art.

Example 3

Entropy Analysis of Ultrasound Images

Figure 4:
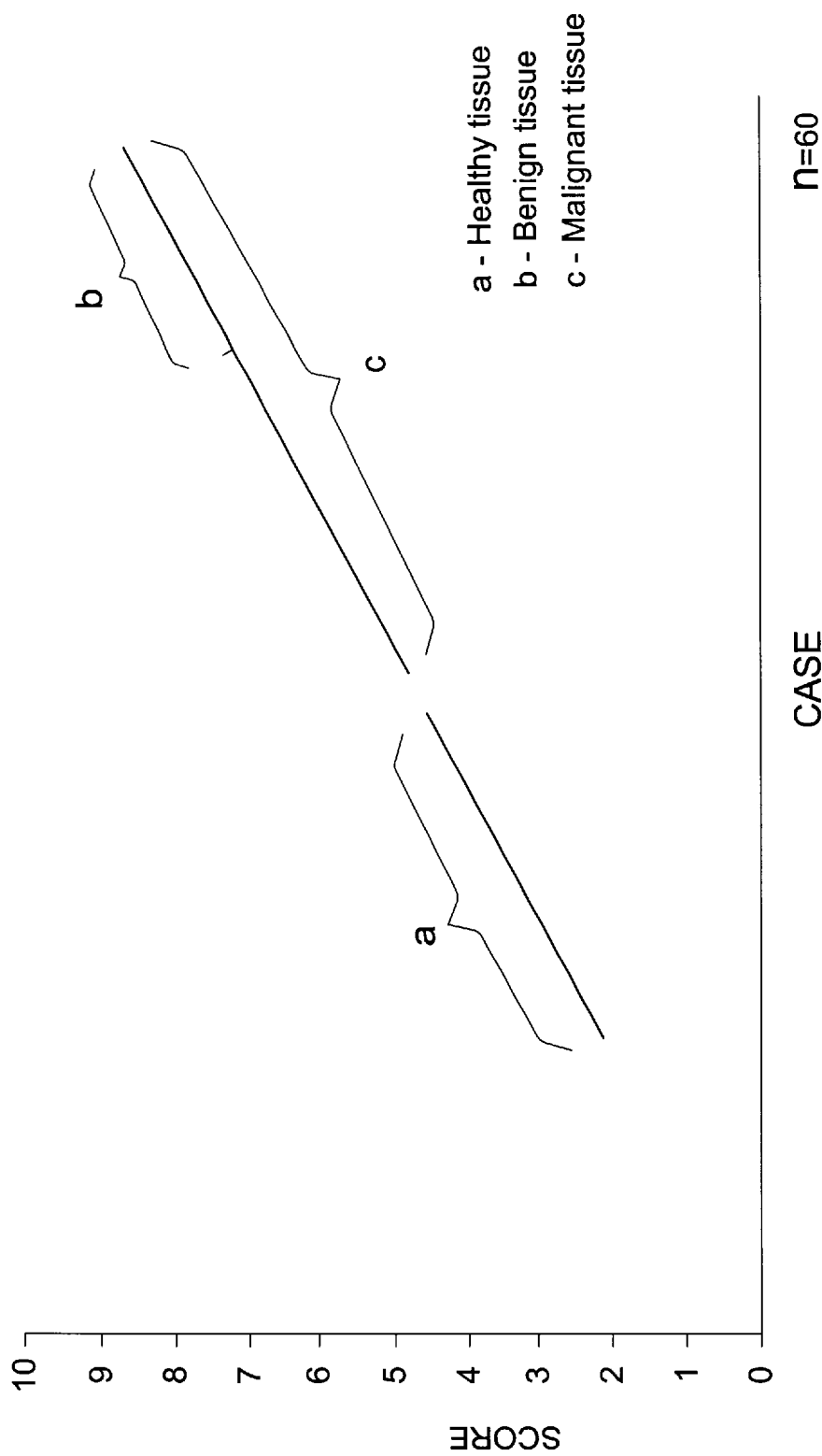
FIG. 4 shows an entropy analysis of healthy malignant and benign ovarian tissue.

FIG. 4 shows the results of an analysis of entropy in 60 images of ovaries. The state (healthy, benign or malignant) was determined for each ovary by histological methods. For each image, a 30×30 pixel square was selected and an entropy E was calculated for each square as follows. For each pixel I(x,y), a parameter A(x,y) was calculated by $$A(x, y) = \frac{1}{n} \sum \left| I(x, y) - I(x', y') \right|^2$$

was calculated, where the sum extends over all pixels (x',y') in the square neighboring the pixel (x,y), and n is the number of pixels neighboring the pixel (x,y). The entropy was then calculated as the average of the A(x,y) over the entire square. As shown in FIG. 4, images of healthy ovaries were found to have the lowest entropy (in the range of 2 to 4.3). Images from malignant ovaries have high entropies (6.9–8.3). Images from benign tissues have intermediate to high values of entropy (4.9–8.3).

What is claimed is:

1. A method for assessing spatial disorder of reflecting members in a tissue, comprising the steps of:

(a) irradiating the tissue;

(b) detecting waves reflected or transmitted by the tissue;

(c) calculating in a space domain one or more parameters indicative of a degree of spatial disorder of reflecting members in the tissue based upon the reflected or transmitted waves wherein the one or more parameters are obtained in a calculation based upon complex raw data obtained from the detected reflected waves; and (d) comparing the one or more parameters to a predetermined threshold to determine the spatial disorder.

2. The method according to claim 1 wherein the tissue is irradiated with sonic radiation.

3. The method according to claim 2 wherein the tissue is irradiated by an ultrasound procedure.

4. The method of claim 1 wherein the one or more parameters are obtained in a calculation involving an analysis selected from the group consisting of:

(a) a Fourier analysis of the complex raw data;

(b) a wavelet analysis of the complex raw data; and (c) an entropy analysis of the complex raw data.

5. The method of claim 1 further comprising step of generating an image of the tissue based upon the detected reflected waves and wherein the one or more parameters are obtained in a calculation based upon the image.

6. The method of claim 5 wherein the parameter is obtained in a calculation involving an analysis selected from the group consisting of (a) Fourier analysis of the image;

(b) a wavelet analysis of the image; and (c) an entropy analysis of the image.

7. The method according to claim 1, wherein the tissue is irradiated with electromagnetic radiation.

8. The method according to claim 7, wherein the tissue is irradiated in a procedure selected from the group consisting of:

(a) a CT procedure; and (b) a MRI procedure.

9. A system for assessing a spatial disorder of reflecting members in a tissue, comprising:

(a) a wave source configured to irradiate the tissue;

(b) a wave detector configured to detect waves reflected by the tissue; and (c) a processor configured to calculate a parameter indicative of a degree of spatial disorder of reflecting members in the tissue based upon the reflected waves; wherein the parameter is obtained in a calculation based upon complex raw data obtained from the detected reflected waves.

10. The system of claim 9 wherein the wave source is configured to irradiate the tissue with sonic radiation.

11. The system of claim 10 configured to carry out an ultrasound procedure.

12. The system of claim 9 wherein the parameter is obtained in a calculation involving an analysis selected from the group consisting of:

(a) a Fourier analysis of the complex raw data;

(b) a wavelet analysis of the complex raw data; and (c) an entropy analysis of the complex raw data.

13. The system of claim 9 wherein the processor is further configured to generate an image of the tissue based upon the detected reflected waves and wherein the parameter is obtained in a calculation based upon the image.

14. The system of claim 13 wherein the parameter is obtained in a calculation involving an analysis selected from the group consisting of:

(a) a Fourier analysis of the image;

(b) a wavelet analysis of the image; and (c) an entropy analysis of the image.

15. The method according to claim 9, wherein the tissue is irradiated with electromagnetic radiation.

16. The method according to claim 15, wherein the tissue is irradiated in a procedure selected from the group consisting of:

(a) a CT procedure; and (b) an MRI procedure.

* * * * *